US006617280B2

(12) United States Patent
Fafchamps et al.

(10) Patent No.: US 6,617,280 B2
(45) Date of Patent: Sep. 9, 2003

(54) CONTINUOUS PROCESS FOR THE PREPARATION OF A STABLE HERBICIDAL AQUEOUS SUSPENSION CONCENTRATE COMPOSITION

(75) Inventors: Jean-Paul Fafchamps, Quaedypre (FR); Jean-Michel Villanueva, Mougins (FR)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/938,371

(22) Filed: Aug. 24, 2001

(65) Prior Publication Data

US 2002/0128154 A1 Sep. 12, 2002

Related U.S. Application Data

(60) Provisional application No. 60/228,316, filed on Aug. 25, 2000.

(51) Int. Cl.$^7$ .......................... A01N 25/04; A01N 33/18

(52) U.S. Cl. ........................ 504/127; 504/130; 504/139; 504/145; 504/347

(58) Field of Search ................................ 504/347, 127, 504/145, 130, 139, 118

(56) References Cited

U.S. PATENT DOCUMENTS

| | | | | | |
|---|---|---|---|---|---|
| 4,571,088 | A | * | 2/1986 | Frensch et al. | 366/136 |
| 4,871,392 | A | | 10/1989 | Morgan et al. | 71/121 |
| 5,147,412 | A | * | 9/1992 | Klinksiek et al. | 23/293 R |
| 5,290,751 | A | * | 3/1994 | Fiard et al. | 504/116 |
| 5,624,884 | A | | 4/1997 | Morgan et al. | 504/148 |

* cited by examiner

*Primary Examiner*—S. Mark Clardy
(74) *Attorney, Agent, or Firm*—Keil & Weinkauf

(57) ABSTRACT

The present invention provides a continuous process for the preparation of a stable aqueous suspension concentrate composition of pendimethalin, alone or in combination with another pesticide, which comprises mixing a molten stream of pendimethalin with a cold aqueous stream containing coformulants plus seed crystals of orange pendimethalin.

12 Claims, No Drawings

CONTINUOUS PROCESS FOR THE PREPARATION OF A STABLE HERBICIDAL AQUEOUS SUSPENSION CONCENTRATE COMPOSITION

This application claims priority from copending provisional application(s) serial No. 60/228,316 filed on Aug. 25, 2000.

BACKGROUND OF THE INVENTION

Stable aqueous suspension concentrate compositions of pendimethalin, alone or in combination with a secondary herbicide, and methods for their preparation are described in U.S. Pat. No. 5,624,884. However, the methods so described are 2-step methods wherein the first step is the formation of a hot aqueous emulsion of molten pendimethalin and the second step is the cooling of said emulsion to crystallize the pendimethalin and form an aqueous suspension concentrate. Optionally, a third milling step may be added. The discreet steps of forming a hot emulsion, then cooling said emulsion and optionally milling said cooled emulsion, entail a non-integrated batch procedure. That is the desired product must be produced in discreet batches of a fixed quantity and the process must begin, end and start again, repeatedly. Such batch processes, when producing quantities on a manufacturing scale can be time-consuming, and labor and energy intensive.

Therefore, it is an object of this invention to provide a single-step continuous process suitable for the preparation of a stable herbicidal aqueous suspension concentrate composition on a manufacturing scale.

It is an advantage of this invention that said stable herbicidal compositions may be prepared efficently and effectively with reduced time, labor and energy resources.

SUMMARY OF THE INVENTION

The present invention provides a process for the preparation of an aqueous suspension concentrate composition which comprises mixing a molten pendimethalin stream having a temperature of about 57° to 75° C. with an aqueous stream containing coformulants plus seed crystals of orange pendimethalin said aqueous stream having a temperature of about −3° C. to 5° C.

DETAILED DESCRIPTION OF THE INVENTION

Pendimethalin is a low-melting dinitroaniline herbicide useful in agricultural, horticultural and turf applications. In its solid form, pendimethalin exists primarily in two polymorphic forms, generally referred to as the orange form and the yellow form. It is known that compositions containing crystalline pendimethalin in 100% of the orange form or in a ratio of 96:4 of the orange form to the yellow form demonstrate enhanced stability. However, control of the poylmorph ratio of pendimethalin in a process involving the conversion of molten pendimethalin to solid pendimethalin is known to be difficult. U.S. Pat. No. 5,624,884 describes stable aqueous suspension concentrate compositions of pendimethalin and methods for their preparation. However, said methods require a two-step procedure which necessitates a batch production effort.

Surprisingly it has now been found that a stable aqueous suspension concentrate composition of pendimethalin may be prepared in a continuous single-step procedure which comprises the high shear mixing of a molten pendimethalin stream, having a temperature of about 57° to 75° C., with an aqueous stream containing coformulants plus seed crystals of orange pendimethalin, said aqueous stream having a temperature of about −3° C. to 5° C. Advantageously, the process of the invention instantaneously and continuously generates a cool stable aqueous suspension of fine, regular, orange crystals of pendimethalin. The process of the invention may be run continuously by any conventional means such as an in-line high shear disperser/homogenizer. Alternatively, the process may be run in batch fashion, if so desired. The stable herbicidal aqueous suspension concentrate composition produced by the process of the invention may optionally be milled to obtain an average particle size of suspended particles of less than 5–20 microns.

The process of the invention may also be used to prepare stable aqueous suspension concentrate compositions containing pendimethalin in combination with one or more pesticides which are low-melting or water-soluble. For example, an additional water-soluble pesticide may be included in the cooled aqueous stream, prior to the mixing of the two streams.

Compositions produced by the process of the invention typically comprise on a weight to volume basis, about 5.0% to 50.0% pendimethalin; about 0% to 50.0% of one or more additional pesticides which are water soluble; about 3.0% to 30.0% of coformulants, such as surfactants, dispersing agents, wetting agents, antifreeze agents, antifoam agents, suspending agents, thickeners, preservatives or the like; and about 20.0% to 92.0% water.

As used in the specification and claims, the term coformulant designates an ingredient such as: a water-soluble pesticide, i.e. a herbicide, fungicide, insecticide, plant growth regulant, or the like; an antifreeze agent, i.e. ethylene glycol, propylene glycol, glycerine, urea, or the like; an antifoam agent, i.e. silicon, or the like; a suspending agent, i.e. silica, $MgSO_4$, or the like; a thickener, i.e. clay, polyvinyl alcohol, polyvinylpyrrolidone, polyacrylamide, or the like; a preservative, i.e. formaldehyde, methyl or propyl parahydroxybenzoate, sodium benzoate, or the like; a surfactant such as a dispersing agent, a wetting agent or the like; or any standard inert ingredient conventionally used in agricultural suspension concentrate compositions.

Water-soluble pesticides contemplated for use in the process of the invention include herbicides, for example: quaternary salts of amino phosphonic or phosphinic acids such as glyphosate, glufosinate, or the like; substituted phenoxy or benzoic acid salts such as 2,4-D, 2,4-DB, MCPP, MCPA, dicamba, chloramben, or the like; imidazolinones such as imazaquin, imazethapyr, imazamox, imazapic, imazapyr, or the like; or any of the known water-soluble herbicidal agents which possess physical/chemical properties known to be amenable to the preparation of aqueous suspension concentrate compositions. Fungicides, insecticides or plant growth regulants which are water-soluble and possess physical/chemical properties which are amenable to the preparation of aqueous suspension concentrate compositions are also contemplated.

Surfactants (including dispersing agents and wetting agents) suitable for use as a coformulant in the process of the invention include: ethylene oxide/propylene oxide condensates; alkylaryl- or arylarylethoxylates or derivatives thereof; lignosulfonates; cresol- or naphthalene-formaldehyde condensates or the sulfonates thereof; polycarboxylates or derivatives thereof; or mixtures thereof. Preferred surfactants are: anionic polymerics, such as mixtures of alkylaryl- or arylarylethoxylates or their derivatives;

cresol formaldehyde condensates or their sulfonates; naphthalene formaldehyde condensates or their sulfonates; or lignosulfonates. More preferred surfactants are mixtures of alkyl, aryl- and arylarylethoxylates or their derivatives.

Accordingly, stable aqueous suspension concentrate compositions of pendimethalin may be prepared by high-shear mixing of a stream of molten pendimethalin having a temperature of about 57° to 75° C. with an aqueous stream containing co-formulants plus orange pendimethalin seed crystals said aqueous stream having a temperature of about −3° to 5° C. In actual practice, a molten stream of technical pendimethalin at 57° to 75° C. is continuously fed into a high-shear disperser/homogenizer simultaneously with an aqueous stream containing coformulants and about 16–24% of orange pendimethalin seed crystals, the aqueous stream having been pre-cooled to temperatures of about −3° C. to 5° C. to produce a continuous exit stream of a stable aqueous suspension concentrate composition of pendimethalin. By continuously, simultaneously feeding and mixing the molten pendimethalin and cooled aqueous streams in an in-line disperser/homogenizer while continuously discharging the resulting orange suspension concentrate composition, the process of the invention facilitates optimum production with significantly increased conservation of time, labor and energy resources. Optionally, the thus-produced suspension concentrate may be bead-milled at 20–29° C. to achieve a particle size of less than 5–20 microns.

Water-soluble pesticides may be co-formulated with pendimethalin using the process of the invention by dissolving said pesticide in the aqueous stream containing coformulants plus orange pendimethalin seed crystals prior to mixing with the molten pendimethalin stream.

Beneficially, compositions produced by the process of the invention do not form large, elongated crystals after being processed. Therefore, processing and manufacturing is not halted because of aggregation due to crystal growth. Further, the agronomic application and efficacy of the suspension concentrate product is not hampered nor compromised by uneven particle size, sedimentation, or crystal growth.

For a more clear understanding of the invention, the following examples are set forth below. These examples are merely illustrative and are not understood to limit the scope or underlying principles of the invention in any way. Indeed, various modifications of theinvention, in addition to those shown and describedgerein, will become apparent to those skilled in the art from the following examples and the foregoing description. Such modifications are also intended to fall within the scope of the appended claims.

Unless otherwise noted, all parts are parts by weight.

EXAMPLES 1–7

Preparation of Stable Aqueous Suspension Concentrate Compositions of Pendimethalin An aqueous stream containing coformulants and 16–24% of orange crystalline pendimethalin is pre-cooled to temperatures of −3° C. to 5° C. and mixed in a high-shear disperser/homogenizer with a stream of molten pendimethalin at temperatures of 57° C. to 75° C. to yield a concentrated aqueous suspension of orange crystalline pendimethalin.

Using the above procedure, the aqueous suspension concentrate compositions shown on Table I are obtained.

TABLE I

|  | 1 | 2 | 3 | 4 | 5 | 6 | 7 |
|---|---|---|---|---|---|---|---|
| Pendimethalin | 30.0 | 33.0 | 40.0 | 40.0 | 40.0 | 40.0 | 33.0 |
| Imazaquin | 5.0 | — | — | — | — | — | — |
| Na+ cresol-formaldehyde condensate | — | — | — | 4.7 | — | — | — |
| Na+ cresol-formaldehyde sulphonated condensate | — | — | 4.2 | — | — | — | 4.2 |
| Triethanolamine salt of polyarylarylethox-ylate phosphate | — | 3.4 | — | — | — | — | — |
| Na+ lignosulfonate | 4.0 | — | — | — | 4.8 | — | — |
| Acetic acid to pH 7.4 | * | — | — | — | — | — | — |
| Polycarboxylate derivative | — | — | — | — | — | 3.0 | — |
| Urea | — | — | — | — | — | — | 13.3 |
| Precipitated silica | 0.75 | — | — | — | — | — | — |
| Xanthum gum | 0.1 | 0.1 | 0.1 | 0.1 | 0.1 | 0.2 | 0.16 |
| Formaldehyde 38% solution | 0.25 | 0.25 | 0.25 | 0.25 | 0.25 | 0.5 | 0.4 |
| Siliconic antifoam | 0.5 | 0.1 | 0.5 | 0.9 | 0.3 | 1.0 | 0.3 |
| Ethylene glycol | 8.0 | 8.0 | 8.0 | — | — | 5.0 | — |
| Ethylene oxide/propylene oxide condensate |  |  |  |  |  |  |  |
| Water | QS | QS | QS | QS | QS | QS | QS |

What is claimed is:

1. A process for the preparation of a stable aqueous suspension concentrate composition which comprises mixing a molten pendimethalin stream having a temperature of about 57° to 75° C. with an aqueous stream containing coformulants plus seed crystals of orange pendimethalin said aqueous stream having a temperature of about −3° C. to 5° C.

2. The process according to claim 1, wherein said seed crystals are present at about 16% to 24%.

3. The process according to claim 1 wherein said coformulants are selected from the group consisting of a surfactant; an antifreeze agent; an antifoam agent; a suspending agent; a thickener; a preservative; a water-soluble pesticide; and a mixture thereof.

4. The process according to claim 3 wherein said surfactant is selected from the group consisting of an ethylene oxide/propylene oxide condensate; an alkylaryl- or arylarylethoxylate; a lignosulfonate; a cresol-formaldehyde condensate or a sulfonate thereof; a naphthalene-formaldehyde condensate or a sulfonate thereof; a polycarboxylate or a derivative thereof; and a mixture thereof.

5. The process according to claim 3 wherein the surfactant is selected from the group consisting of an alkylarylethoxylate; a triethanolamine salt or a potassium salt of polyarylarylethoxylate phosphate; a polyarylarylpolyoxyethylene phosphoric acid; a sodium cresol-formaldehyde condensate; a sodium salt of a sulfonated cresol-formaldehyde condensate; and a mixture thereof.

6. The process according to claim 3 wherein the antifreeze agent is selected from the group consisting of ethylene glycol; propylene glycol; glycerine; urea; and a mixture thereof.

7. The process according to claim 3 wherein the thickener is selected from the group consisting of clay; precipitated silica; polyvinyl alcohol; polyvinylpyrrolidone; polyacrylamide; and a mixture thereof.

8. The process according to claim 3 wherein the preservative is selected from the group consisting of a 38% formaldehyde solution; methyl or propyl parahydroxybenzoate; 2-bromo-2-nitropropane-1,3-diol; sodium benzoate; glutaraldehyde; o-phenylphenol; benzisothiazolinone; methyl or ethyl 4-isothiazolin-3-one; pentachlorophenol; 2,4-dichlorobenzyl alcohol; and a mixture thereof.

9. The process according to claim 8 wherein the preservative is a 38% formaldehyde solution.

10. The process according to claim 3 wherein the water-soluble pesticide is a water-soluble herbicide.

11. The process according to claim 10 wherein said herbicide is selected from the group consisting of a quaternary salt of an amino phosphonic or phosphinic acid; a substituted phenoxy or benzoic acid salt; an imidazolinone; and a mixture thereof.

12. The process according to claim 11 wherein said herbicide is selected from the group consisting of glyphosate; glufosinate; 2,4-D; MCPA; dicamba; imazaquin; imazethapyr; imazapic; imazamox; imazapyr; and a mixture thereof.

* * * * *